United States Patent [19]

Rouse

[11] Patent Number: 5,006,066

[45] Date of Patent: Apr. 9, 1991

[54] AUTOCLAVABLE DENTAL BURR HOLDER

[76] Inventor: Melvin R. Rouse, 1056 Serpentine La., Pleasanton, Calif. 94566

[21] Appl. No.: 312,137

[22] Filed: Feb. 17, 1989

[51] Int. Cl.$^5$ .............................................. A61G 15/00
[52] U.S. Cl. ...................................... 433/77; 206/369; 206/379
[58] Field of Search ........................... 433/77, 79, 165; 206/368, 369, 379

[56] References Cited

U.S. PATENT DOCUMENTS

| 1,043,891 | 11/1912 | Zange | 206/379 |
| 2,902,170 | 9/1959 | Miller | 206/379 |
| 3,904,035 | 9/1975 | Metzler et al. | 206/379 |

FOREIGN PATENT DOCUMENTS

| 0242079 | 8/1965 | Austria | 206/379 |
| 0485363 | 8/1952 | Canada | 206/379 |

Primary Examiner—Robert P. Swiatek
Assistant Examiner—Adriene B. Lepiane
Attorney, Agent, or Firm—Roy A. Ekstrand

[57] ABSTRACT

A dental burr holder includes an elongated burr block defining a cylindrical lateral base and a plurality of upwardly extending generally cylindrical bore supports molded in a single unit. The burr supports each define respective bores extending downwardly therein configured to receive a plurality of dental burrs. A generally U-shaped burr cover is formed of a resilient material and defines a pair of inwardly extending faceted bosses at the lower ends of each of the burr cover end pieces. The cylindrical base of the burr block defines corresponding faceted recesses which receive the faceted bosses to provide a detented attachment between the burr block cover and the burr block. The relative position between the burr block cover and the burr block may be varied by detented rotation therebetween.

16 Claims, 1 Drawing Sheet

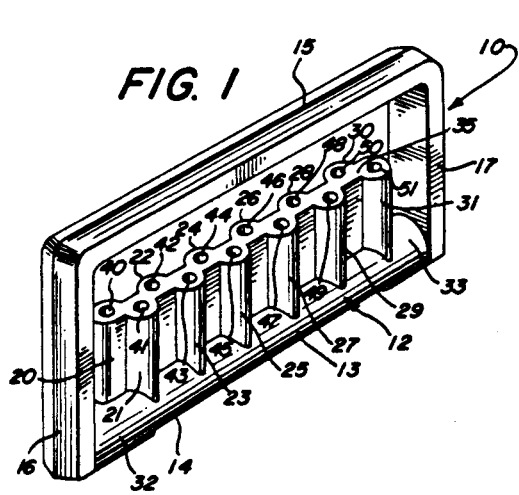
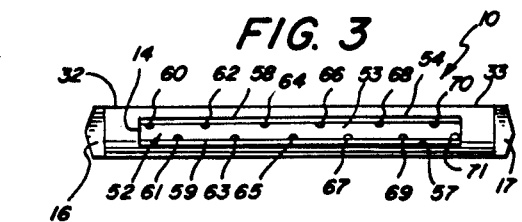
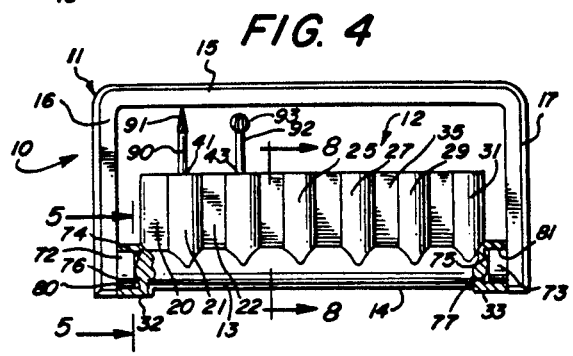
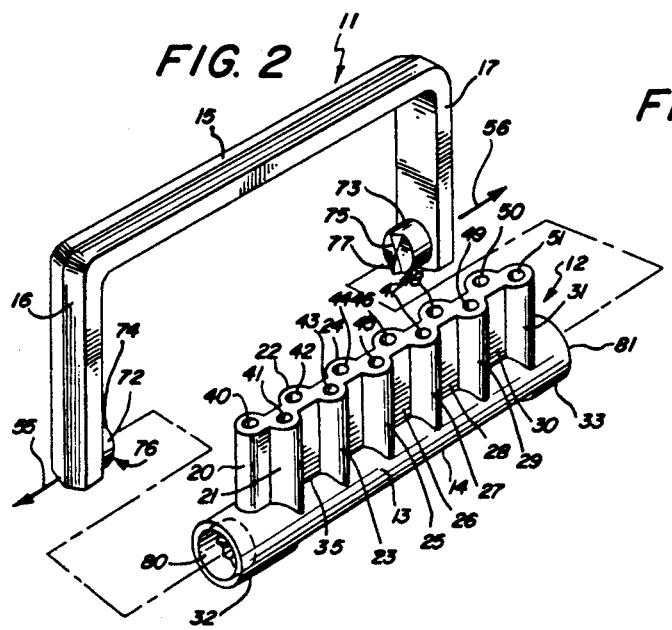
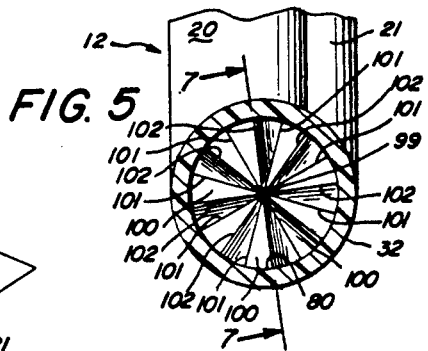
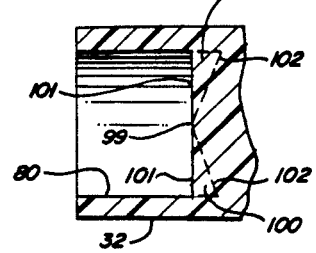
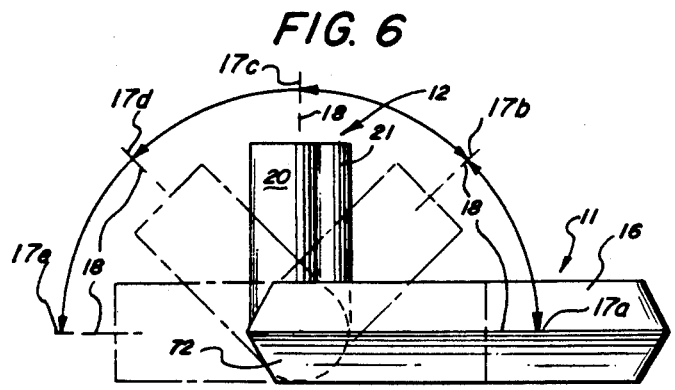
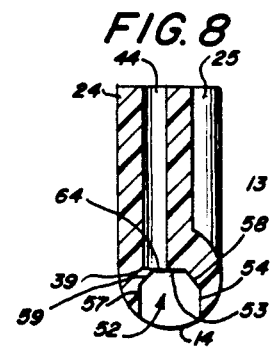

AUTOCLAVABLE DENTAL BURR HOLDER

FIELD OF THE INVENTION

This invention relates generally to dental drill technology and particularly to devices utilized to hold and store dental drill bits during cleaning and use.

BACKGROUND OF THE INVENTION

Through the years a great number of dental drill designs and improvements have been provided by those skilled in the art to reduce patient pain and improve the quality of dental work. One of the most substantial and far reaching of such improvements is the development of the new turbine-type high speed dental drills. While the structures of such high speed dental drills have undergone some change and variation, all generally include an elongated holder which supports a rotatable chuck and an internal turbine wheel. Passages within the holder are coupled to a source of high pressure air or water and are structured to direct pressurized air or water at the turbine thereby rotating the chuck at high speed. The chuck removably supports interchangeable dental drill bits generally known in the art as "burrs". Such dental burrs are produced in a variety of shapes and sizes but generally all include a common sized cylindrical shank adapted to be interchangeably received within the drill chuck together with tapered extensions which terminate in a small cutting end. The cutting ends of the dental burrs are produced in a variety of shapes such as spherical, elongated, cylindrical, or otherwise.

Because dental burrs are capable of repeated use on successive patients, they must be cleaned and sanitized repeatedly and frequently. Most common among the cleaning processes employed involves the sanitizing of the drill burrs within an autoclave or similar device. Autoclaves provide a high temperature cleansing environment in which the dental burrs are subjected to extremely high temperatures selected to be sufficient to destroy any existing bacteria or organisms otherwise present on the dental burrs. Since dental burrs are expensive and often delicate, great care must be taken to avoid damaging them during the cleaning and sanitizing operation and during the periods of handling, storing and use. Of particular concern in avoiding damage to the dental burrs is the protection of the delicate cutting ends thereof.

The general need to secure and protect such dental burrs and similar objects during cleansing, handling, storing, and use has prompted practitioners in the art to provide a number of different storage and support structures for such objects.

One such structure is set forth in U.S. Pat. No. 2,902,170 issued to Miller which sets forth a TEST TUBE RACK in which a generally rectangular support structure includes a frame having parallel side supports, a bottom support, and a pair of laterally extending cross members. Each of the cross members define a plurality of holes adapted to receive and retain conventional test tubes within the frame. A pair of pivotally secured handle members are attached to the frame side portions and are rotatable to outwardly extending support positions and alternatively to closed positions captivating the test tubes within the frame.

U.S. Pat. No. 4,306,862 issued to Knox sets forth a DENTAL BURR TOOL BLOCK in which a housing defines a plurality of bore openings for receiving and storing a variety of dental burr tools. A reservoir compartment defined within the block is capable of supporting a volume of disinfectant fluid and a drain hole in the reservoir compartment permits removal of the disinfectant fluid. A separate compartment within the burr tool block receives and supports a burr changer tool. A protective covering formed of a transparent material is pivotally secured to the burr tool block to provide a dust cover enclosure for the dental burrs.

U.S. Pat. No. 2,584,721 issued to Linneman sets forth a CASE WITH SPRING-URGED PIVOTED SLIDING CLOSURE in which a vertically oriented support base defines a plurality of vertical bores adapted to receive a plurality of elongated objects such as drills. A pair of covering members provide a claw-like closure for the vertical housing which is alternately positionable in a closed position above the housing captivating and enclosing the drill bits and an open position in which the members are forced downwardly and are opened to rest on either side of the housing and provide open access to the supported drill bit.

U.S. Pat. No. 3,904,035 issued to Metzler, et al. sets forth a RECEPTACLE WITH HINGED CLOSURE FLAPS in which a receptacle for storing long articles includes a generally rectangular container having article receiving openings at one end. A pair of hinged cover flaps are pivotally secured to the housing and are alternatively positionable in a closed position in which the closure flaps enclose and captivate the article receiving openings and an open end in which the closure flaps are locked open providing access to the receptacle.

SUMMARY OF THE INVENTION

Accordingly, it is a general object of the present invention to provide an improved dental burr holder. It is a more particular object of the present invention to provide an improved dental burr holder suitable for use in high temperature cleaning and sterilizing environments. It is a still more particular object of the present invention to provide an improved dental burr holder which functions to protect the delicate dental burr cutting ends and which provides a convenient holder for supporting the dental burrs between uses.

In accordance with the present invention, there is provided for use in holding a plurality of dental burrs each having elongated shaft portions and cutting ends, a dental burr holder comprising an elongated burr block defining a plurality of bores for receiving the shaft portions of dental burrs such that the cutting ends thereof extend beyond the bores, and a plurality of drain passages extending from the bores, a burr block cover having a cross member extending transverse to the first direction and a pair of side members; and detent support means coupling the side members to the burr block in a detented rotatable attachment.

BRIEF DESCRIPTION OF THE DRAWINGS

The features of the present invention, which are believed to be novel, are set forth with particularity in the appended claims. The invention, together with further objects and advantages thereof, may best be understood by reference to the following description taken in conjunction with the accompanying drawings, in the several figures of which like reference numerals identify like elements and in which:

FIG. 1 is a perspective view of the present invention dental burr holder;

FIG. 2 is a perspective assembly view of the present invention dental burr holder;

FIG. 3 is a bottom view of the present invention dental burr holder;

FIG. 4 is a partially sectioned side view of the present invention dental burr holder;

FIG. 5 is a partial section view of a portion of the present invention dental burr holder taken along section lines 5—5 in FIG. 4;

FIG. 6 is an end view of the present invention dental burr holder in the open position;

FIG. 7 is a section view of a portion of the present invention dental burr holder taken along section lines 7—7 in FIG. 5; and FIG. 8 is a section view of the present invention dental burr holder taken along section lines 8—8 in FIG. 4.

DESCRIPTION OF THE PREFERRED EMBODIMENT

FIG. 1 sets forth a perspective view of a dental burr holder constructed in accordance with the present invention and generally referenced by numeral 10. Burr holder 10 includes an elongated burr block 12 defining an elongated cylindrical base 13 having end portions 32 and 33 thereon and a notch portion 14. Burr block further defines a plurality of upwardly extending generally cylindrical burr supports 20 through 31 extending from cylindrical base 13 between end portions 32 and 33 respectively. Burr supports 20 through 31 are alternately offset such that burr supports 20, 22, 24, 26, 28 and 30 are interleaved with burr supports 21, 23, 25, 27, 29 and 31. A connecting web 35 interconnects burr supports 20 through 31 and is joined to cylindrical base 13 to provide rigid support of burr supports 20 through 31. In addition, burr supports 20 through 31 define cylindrical bores 40 through 51 respectively which, as described below, extend downwardly within their respective burr supports to provide a supporting passage for receiving a corresponding plurality of dental burrs (the latter better seen in FIG. 4).

A burr block cover 11 is formed of a generally U-shaped member having a cross member 15 supported by a pair of side members 16 and 17. Side members 16 and 17 are, of by means set forth below in greater detail, rotatably attached to ends 32 and 33 of cylindrical base 13 such that burr block cover 11 is rotatable with respect to burr block 12. In addition, it should be noted that side members 16 and 17 are of sufficient length to support cross member 15 above burr supports 20 through 31 in a spaced apart generally parallel relationship. While a variety of materials may be used to fabricate burr holder 10, in its preferred form, burr block 12 and burr cover 11 are molded of a high temperature resin having glass fiber reinforcement.

FIG. 2 sets forth a perspective assembly view of burr holder 10 showing burr block cover 11 and burr block 12 separated prior to assembly. As described above, burr block 12 defines a generally cylindrical base 13 having end portions 32 and 33 and a plurality of upwardly extending generally cylindrical burr supports 20 through 31. As is also described above, burr supports 20 through 31 are secured by a transversely extending connecting web 35. Burr supports 20 through 31 each define cylindrical bores 40 through 51 respectively which receive dental burrs such as burrs 90 and 92 in FIG. 4. Cylindrical base 13 further defines an extending notch 14 and a pair of faceted recesses 80 and 81. The latter are shown in greater detail in FIGS. 4 and 5. However, suffice it to note here that faceted recesses 80 and 81 define generally cylindrical recesses having closed end portions within ends 32 and 33 respectively of cylindrical base 13. It should be further noted that faceted recesses 80 and 81 define a radially arranged plurality of facets described below in greater detail.

Burr block cover 11, as described above, is formed of a single molded unit having a cross member 15 and a pair of side members 16 and 17 arranged in a generally U-shaped configuration. In addition, side member 16 defines an inwardly extending generally cylindrical faceted boss 72 having a pair of wedged teeth 74 and 76 extending inwardly therefrom. Correspondingly, side member 17 defines a similar inwardly extending cylindrical faceted boss 73 having a pair of wedged teeth 75 and 77 extending inwardly therefrom. In accordance with an important aspect of the present invention, burr block cover 11 is assembled to burr block 12 by forcing side members 16 and 17 outwardly in the directions indicated by arrows 55 and 56 respectively to expand burr block cover 11 until faceted bosses 72 and 73 are spaced apart a sufficient distance to permit faceted bosses 72 and 73 to be aligned with faceted recesses 80 and 81 respectively. Thereafter, the outward force on side members 16 and 17 is released and the resilient character of burr block 11 drives faceted bosses 72 and 73 into faceted recesses 80 and 81 respectively which in turn secures burr block cover 11 to burr block 12.

In the alternative, burr block cover 11 may be formed of a more rigid high strength material and the assembly of burr block 11 to burr block 12 may be carried forward with less outward expansion of side members 16 and 17 by initially inserting one of the faceted bosses such as faceted boss 72 within faceted recess 80 and thereafter extending side member 17 outwardly in the direction indicated by arrow 56 until faceted boss 73 may pass beyond end 33 and into alignment with faceted recess 81. Thereafter, the outward force on side member 17 is released and the spring force of burr block cover 11 causes faceted boss 73 to be inserted within faceted recess 81.

In either event, the assembly of burr block cover 11 to burr block 12 is accomplished with a minimum of parts and without the use of additional fastening devices. In accordance with an important aspect of the present invention and as described below in greater detail, wedged teeth 74 and 76 of faceted boss 72 cooperate with the plurality of facets within faceted recess 80 to provide a detented action therebetween. Correspondingly, wedged teeth 75 and 77 of faceted boss 73 cooperate with the plurality of facets within faceted recess 81 to provide a corresponding detented rotatable attachment. As a result and by means described below in greater detail, burr block cover 11 is secured to burr block 12 in a rotatable detented attachment which permits multiple positioning of burr block cover 11 with respect to burr block 12 (shown in FIG. 6). It should be noted that the entire structure of burr holder 10 is provided with two molded members and requires no additional parts.

FIG. 3 sets forth a bottom view of burr holder 10 showing cylindrical base 13 having ends 32 and 33 and defining an elongated notch 14 assembled to side members 16 and 17 of burr block cover 11. As mentioned above, notch 14 extends between end portions 32 and 33 of cylindrical base 13. Notch 14 defines an elongated generally rectangular recess 52 having a pair of inwardly extending side walls 54 and 57 and a closed end surface 53. Recess 52 further defines a pair of angled surfaces 58 and 59 and a plurality of drain passages 60 and through 71 which extend through surface 53. As is better seen with temporary reference to FIG. 8, drain passages 60 through 71 respectively extend to bores 40 through 51 respectively providing drain passages by which liquid within bores 40 through 51 are able to flow downwardly through drain passages 60 through 71 respectively and outwardly through recess 52 of notch 14.

FIG. 4 sets forth a partially sectioned side view of burr holder 10 showing burr block cover 11 in the closed position. Burr block 12 defines a cylindrical base 13 having end portions 32 and 33 which, as described above, define faceted recesses 80 and 81 respectively. As is also described above, a plurality of burr supports 20 through 31 and a supporting web 35 extend upwardly from cylindrical base 13. Burr block cover 11 defines a cross member 15 and a pair of side members 16 and 17. The latter describe inwardly extending faceted bosses 72 and 73 which are received within faceted recesses 80 and 81 respectively. As mentioned above, faceted bosses 72 and 73 are retained within faceted recesses 80 and 81 respectively by the spring force of burr block cover 11.

As is also mentioned above, burr supports 20 through 31 define respective bores 40 through 51 extending downwardly therethrough. In accordance with an important aspect of the present invention, a plurality of dental burrs may be received within bores 40 through 51 and secured therein by the covering of cross member 15 of burr block cover 11. By way of example, a pair of typical dental burrs 90 and 92 are shown received within bores 41 and 43 of burr supports 21 and 23 respectively. In accordance with typical dental burr construction, dental burrs 90 and 92 define respective cutting tips 91 and 93. As will be apparent from examination of FIGS. 1 and 4, dental burrs 90 and 92 are captivated within bores 41 and 43 respectively by the covering of cross member 15 of burr block cover 11. It should also be noted that some clearance is provided between cutting ends 91 and 93 of dental burrs 90 and 92 and cross member 15. As mentioned above, burr block cover 11 is preferably formed of a molded plastic or resin material having reinforcing glass fibers therein. In accordance with a further important aspect of the present invention, the material selected to fabricate burr block cover 11 is sufficiently soft to avoid damage to the delicate cutting ends of dental burrs supported within bores 40 through 51. In the example shown in FIG. 4, cutting ends 91 and 93 of dental burrs 90 and 92 are protected by cross member 15 of burr block cover 11. Cutting ends 91 and 93 are not damaged by contact with the softer material of cross member 15 and thus damage thereto is avoided during the storage, cleaning and transport of dental burrs within burr cover 10. While FIG. 4 shows a pair of dental burrs supported within burr holder 10, it will be apparent to those skilled in the art that each of bores 40 through 51 is capable of receiving and supporting a dental burr and that, in the structure shown in FIG. 4, a total of twelve dental burrs may be simultaneously supported within burr holder 10. It will be equally apparent to those skilled in the art that the selection of the number of burr supports in burr holder 10 is a matter of design choice and that burr holders of similar structure accommodating a different number of burr supports may be fabricated without departing from the spirit and scope of the present invention.

FIG. 5 sets forth a partial section view of the present invention burr holder taken along section lines 5—5 in FIG. 4. In particular, FIG. 5 sets forth the structure of end 32 of burr block 12 which, as described above, defines a pair of upwardly extending burr supports 20 and 21 as well as a faceted recess 80. Faceted recess 80 defines a cylindrical recess terminating in a plurality of triangular shaped radially disposed facets 100. Facets 100 are of substantially identical shape and symmetrically disposed about recess 99. In addition, facets 100 are alternately angled to form a radial succession of peaks 101 separated by valleys 102.

With temporary reference to FIG. 2 and as is particularly well shown in the depiction of faceted boss 73, the shape of wedged teeth 75 and 77 is configured to be received within valleys 102 of faceted recess 81. A similar compatibility exists between faceted boss 72, wedged teeth 74 and 76, and faceted recess 80. Thus, the attachment of burr block cover 11 to burr block 12 is maintained solely by the captivation of faceted bosses 72 and 73 within faceted recesses 80 and 81. Concurrently, the resilient character of burr block cover 11 provides a retaining spring which permits the rotation of burr block cover 11 with respect to burr block 12 while the cooperation of teeth 74 and 76 of faceted boss 72 and teeth 75 and 77 of faceted boss 73 cooperate with the faceted structures of recesses 80 and 81 to provide a detented attachment. Thus, at each position in which the wedged teeth of faceted bosses 72 and 73 are received within the valley portions of faceted recesses 80 and 81, a secure detented position of burr block cover 11 with respect to burr block 12 result. The position of burr block cover 11 is changeable by rotating burr block cover 11 with respect to burr block 12 which causes a camming action between the wedged shaped teeth of faceted bosses 72 and 73 and the facets within faceted recesses 80 and 81 which spreads side members 16 and 17 outwardly in opposition to the spring force created by the resilience of burr block cover 11. As burr block cover 11 is further rotated, the wedged teeth of faceted bosses 72 and 73 pass over the peak portions of the faceted recess causing them to be forced into the next valley portions which in turn secures burr block cover 11 in the next detent position.

FIG. 6 sets forth a side view of burr holder 10 in which cover 11 is horizontally positioned while burr block 12 is rotated through a plurality of angular positions in accordance with the detented positioning described above. Accordingly, burr block cover 11 defines a side member 16 having a faceted boss 72 extending inwardly therefrom. Burr block 12 defines upwardly extending burr supports 20 and 21 and is shown in a perpendicular relationship with burr block cover 11. Burr block 12 defines a center axis 18 which, in the position shown in FIG. 6, extends vertically and in a perpendicular orientation to burr block cover 11. In the position shown in FIG. 6, dental burrs may readily be removed from or placed within burr block cover 12 while the entire assembly rests upon burr block cover 11. Thus, FIG. 6 shows the present invention burr holder in its open free standing position. The vertical orientation of burr block cover 12 is maintained in accordance with the above-described detented attachment and is of sufficient strength to adequately support burr block 12 together with a plurality of dental burrs. In the alternative and in accordance with the above-described detented positioning, the relative position of burr block 12 with respect to burr block cover 11 may be varied to the alternate positions shown in dashed-line representation. Specifically, burr block 12 may be rotated from the perpendicular position shown in which center axis 18 is aligned at position 17c by movement in the counterclockwise direction to the angular position shown in which center axis 18 is aligned with angular position 17d. Burr block cover 12 may be further rotated in a counterclockwise direction to a horizontal orientation in which center axis 18 assumes the angular position 17e. In the alternative, burr block 12 may be rotated in the clockwise direction from its vertical position shown in FIG. 6 to the next clockwise detent position in which axis 18 is aligned with angular position 17b. Thereafter, burr block 12 may be further rotated in the clockwise direction until burr block 12 is received within burr cover 11 and axis 18 assumes angular position 17a. The latter corresponds to the closed position shown in FIGS. 1 and 4. In any event, it should be noted that during the multiple positioning of burr block 12, burr block cover 11 provides a suitable support base for burr holder 10.

It will be apparent to those skilled in the art by the examination of the structures of faceted bosses 72 and 73 together with faceted recesses 80 and 81, that burr block 12 may be multiply-positioned in the mirror image positions of those shown in FIG. 6. That is to say, burr block cover 11 is rotatable through a full circle of detented positions with respect to burr block cover 12. This capability permits additional flexibility in the positioning of burr supports 20 through 31 in either a left to right or right to left position while supported by burr block cover 11.

FIG. 7 sets forth a section view of end portion 32 of cylindrical base 13. Cylindrical recess 80 defines a plurality of facets 100 which form valley portions 102 and peak portion 101. As can be seen in FIG. 7, facets 100 are symmetrically positioned with respect to center 99.

FIG. 8 sets forth a section view of the present invention burr holder taken along section lines 8—8 in FIG. 4. As described above, burr block 12 defines upwardly extending cylindrical burr supports 24 and 25. Burr support 24 defines a cylindrical downwardly extending bore 44 which terminate in a closed end 39. Cylindrical base 13 further defines an upwardly extending notch 14 comprising an elongated recess 52 having a pair of upwardly extending side walls 54 and 57 and an upper surface 53. Notch 14 further includes a pair of angled surfaces 58 and 59 joining side walls 54 and 57 respectively to surface 53. A drain passage 64 extends through closed end 39 and communicates bore 44 with recess 52. In accordance with an important aspect of the present invention, drain passage 64 provides a fluid drain path for liquids captivated within bore 44 to drain downwardly through drain passage 64 and out through recess 52. Thus, liquids trapped within bore 44 may drain from any supported dental burr therein to facilitate proper drying and cleansing action. It will be apparent to those skilled in the art that while the detailed structure of burr support 24, bore 44 and drain passage 64 are shown in detail in FIG. 8, the structures of the remaining burr supports 20 through 31 are substantially identical and, in accordance with FIG. 3, each include respective drain passages to provide the above-described liquid draining action.

What has been shown is an improved dental burr holder suitable for use in high temperature cleaning and sterilizing environments. The improved dental burr shown is formed of two major components which are detentably positioned with respect to each other to alternatively captivate and protect dental burrs on the one hand or support a plurality of dental burrs in a convenient holder during use or removal and replacement within the burr holder.

It should be noted that different diameters of bores 40 through 51 may be combined in burr block 12 to accommodate both right angle and straight shaft dental burrs.

While particular embodiments of the invention have been shown and described, it will be obvious to those skilled in the art that changes and modifications may be made without departing from the invention in its broader aspects. Therefore the aim in the appended claims is to cover all such changes and modifications as fall within the true spirit and scope of the invention.

That which is claimed is:

1. For use in holding a plurality of dental burrs each having elongated shaft portions and cutting ends, a dental burr holder comprising:
   an elongated burr block defining a plurality of bores extending into said burr block in a first common direction for receiving the shaft portions of dental burrs such that the cutting ends thereof extend beyond said bores, and a plurality of drain passages extending from said bores in a second common direction;
   a burr block cover having a cross member extending transverse to said first direction and a pair of side members; and
   detent support means coupling said side members to said burr block in a detented rotatable attachment.

2. A dental burr holder as set forth in claim 1 wherein said plurality of bores in said burr block are arranged in a pair of parallel rows.

3. A dental burr holder as set forth in claim 2 wherein said bores in one of said parallel rows are offset from said bores in the other of said parallel rows.

4. A dental burr holder as set forth in claim 3 wherein said burr block defines first and second outwardly extending end portions on each side of said parallel rows of bores and wherein said detent support means include:
   first and second faceted recesses extending into said first and second end portions respectively; and
   first and second faceted bosses extending inwardly from said side members received within said first and second faceted recesses respectively.

5. A dental burr holder as set forth in claim 4 wherein said burr block cover is formed of a resilient material producing an inward spring force to maintain said first and second faceted bosses within said first and second faceted recesses.

6. A dental burr holder as set forth in claim 5 wherein said burr block and said burr block cover are formed of molded resin having glass fibers therein.

7. For use in holding a plurality of dental burrs each of which include elongated shaft portions and cutting ends, a dental burr holder comprising:
   a burr block defining a generally cylindrical base having first and second ends having respective first and second faceted recesses formed therein, a plurality of generally cylindrical burr supports extending upwardly from said cylindrical base, each of said burr supports defining a generally cylindrical bore therein, a coupling web extending between said burr supports; and a burr cover formed of a resilient material and defining a generally U-shaped member having a cross member and first and second supporting side members, said first and second side members defining respective first and second inwardly extending faceted boss, said burr cover being assembled to said burr block by temporarily expanding said burr cover to align said first and second faceted bosses with said first and second faceted recesses respectively and thereafter releasing said burr cover to insert said first and second faceted bosses into said first and second faceted recesses respectively.

8. A dental burr holder as set forth in claim 7 wherein said cross member of said burr cover traverses said bores and is spaced from said burr block.

9. A dental burr holder as set forth in claim 8 wherein said burr supports are of equal length and are supported in a pair of offset parallel arrays.

10. A dental burr holder as set forth in claim 9 wherein said first and second faceted recesses define first and second pluralities of triangular facets each arranged to provide interleaved peaks and valleys and wherein said first and second faceted bosses define first and second wedged portions cooperating with said pluralities of triangular facets to detentably hold said burr cover in a selected one of a plurality of angular positions with respect to said burr block.

11. A dental burr holder as set forth in claim 10 wherein said cylindrical base defines an upwardly extending drain recess aligned with said burr supports and a plurality of drain passages extending from said plurality of bores to said drain recess.

12. A dental burr holder as set forth in claim 11 wherein said burr block and said burr cover are formed of a molded resin having glass fibers therein.

13. For use in holding a plurality of dental burrs each of which include elongated shaft portions and cutting ends, a dental burr holder comprising:

a burr block defining a generally cylindrical base having first and second ends having respective first and second faceted recesses formed therein, a plurality of generally cylindrical burr supports extending upwardly from said cylindrical base, each of said burr supports defining a generally cylindrical bore therein, a coupling web extending between said burr supports; and a burr cover formed of a resilient material and defining a generally U-shaped member having a cross member and first and second supporting side members, said first and second side members defining respective first and second inwardly extending faceted boss, said burr cover being detentably assembled to said burr block by the cooperation of said first and second faceted bosses and said first and second faceted recesses.

14. A dental burr holder as set forth in claim 13 wherein said burr block defines a plurality of drain passages extending from said bores.

15. A dental burr holder as set forth in claim 14 wherein said burr cover is detentable into a position in which said cross member captivates any dental burrs received within said bores and protects the cutting ends thereof.

16. A dental burr holder as set forth in claim 15 wherein said burr cover is detentable into a position in which said burr cover forms a support base for said burr block and dental burrs within said bores may be removed therefrom.

* * * * *